US008187800B2

(12) United States Patent
Mi et al.

(10) Patent No.: US 8,187,800 B2
(45) Date of Patent: May 29, 2012

(54) METHODS FOR SELECTING ACTIVE AGENTS FOR CANCER TREATMENT

(75) Inventors: Zhibao Mi, Pittsburgh, PA (US); Dave Gingrich, Pittsburgh, PA (US); Mike Gabrin, Pittsburgh, PA (US)

(73) Assignee: Precision Therapeutics, Inc., Philadelphia, PA (US)

( * ) Notice: Subject to any disclaimer, the term of this patent is extended or adjusted under 35 U.S.C. 154(b) by 0 days.

(21) Appl. No.: 12/252,073

(22) Filed: Oct. 15, 2008

(65) Prior Publication Data

US 2009/0104647 A1 Apr. 23, 2009

Related U.S. Application Data

(60) Provisional application No. 60/980,098, filed on Oct. 15, 2007.

(51) Int. Cl.
*C12Q 1/00* (2006.01)
(52) U.S. Cl. ............................................................. 435/4
(58) Field of Classification Search ........................ None
See application file for complete search history.

(56) References Cited

U.S. PATENT DOCUMENTS

| | | | | |
|---|---|---|---|---|
| 5,728,541 | A * | 3/1998 | Kornblith | 435/29 |
| 6,416,967 | B2 | 7/2002 | Kornblith | |
| 6,887,680 | B2 | 5/2005 | Kornblith | |
| 6,900,027 | B1 | 5/2005 | Kornblith | |
| 6,933,129 | B1 | 8/2005 | Kornblith | |
| 7,112,415 | B2 * | 9/2006 | Kornblith | 435/29 |
| 7,314,731 | B2 * | 1/2008 | Kornblith | 435/29 |
| 7,501,260 | B2 * | 3/2009 | Kornblith | 435/29 |
| 7,575,868 | B2 * | 8/2009 | Kornblith et al. | 435/6 |
| 7,642,048 | B2 * | 1/2010 | Gabrin et al. | 435/4 |
| 7,678,552 | B2 * | 3/2010 | Kornblith | 435/30 |
| 2005/0084529 | A1 | 4/2005 | Rosenberg | |
| 2006/0211060 | A1 | 9/2006 | Haley et al. | |
| 2007/0037136 | A1 | 2/2007 | Kornblith | |
| 2007/0054330 | A1 | 3/2007 | Brennscheidt et al. | |
| 2007/0059821 | A1 | 3/2007 | Kornblith | |
| 2008/0032298 | A1 | 2/2008 | Kornblith | |
| 2008/0085519 | A1 | 4/2008 | Gabrin et al. | |
| 2009/0042221 | A1 | 2/2009 | Kornblith | |
| 2009/0042225 | A1 | 2/2009 | Kornblith | |

FOREIGN PATENT DOCUMENTS

WO  WO 2006/105255 A2 * 10/2006
WO  WO 2007/028146         3/2007

OTHER PUBLICATIONS

Heinig et al (Rofo, 1997, 166(4): Abstract).*
Knauer et al (Breast Cancer Research Treatment, 2008, 110: 395-396).*
Federico et al (Gynecologic Oncology, 1994, 55(3): Abstract.*
Gardner (Cancer Research, 2000, 60: 1417-1425).*
Heinig et al (Rofo, 1997, 166(4):342-345).*
Federico et al (Gynecol. Oncol, 1994, 55:S156-163).*

The International Search Report issued in International Application No. PCT/US2008/079964 on Jun. 3, 2009, 4 pages.
Breslin et al., "Sentinel Lymph Node Biopsy Is Accurate After Neoadjuvant Chemotherapy for Breast Cancer", Journal of Clinical Oncology, Oct. 2000, vol. 18, No. 20, pp. 3480-3486.
Danesi et al., "Pharmacokinetic-pharmacodynamic relactionships of the Anthracycline Anticancer Drugs", Clin. Pharmacokinet, 2002, vol. 41, No. 6, pp. 431-444.
Goss, Paul E., et al., "Effects of Steroidal and Nonsteroidal Aromatase Inhibitors on Markers of Bone Turnover in Healthy Postmenopausal Women," Breast Cancer Research, Current Science, London, GB., vol. 9, No. 4, Aug. 10, 2007, p. R52.
Staib, P., et al., "Prognosis in Adult AML is Precisely Predicted by the DISC-assay Using the Cemosensitivity-index Ci," Advances in Experimental Medicine and Biology 1999, vol. 457, 1999, pp. 437-444.
Wurz, Gregory T., et al., "Pharmacokinetic Analysis of High-Dose Toremifene in Combination with Duxorubicin," Cancer Chemotherapy and Pharmacology, vol. 42, No. 5, Oct. 1998, pp. 363-366.
Yamashita, T. S., et al., "A Versatile computational Method for the Determination of Areas Under the Curve and Moment Curve Following Multidose Drug Administration," International Journal of Bio-Medical Computing, Elsevier Science Publishers, vol. 23, No. 304, Dec. 1, 1988, pp. 239-249.
Staib, P., et al. "Prediciton of Individual Response to Chemotherapy in Patients With Acute Myeloid Leukaemia Using the Chemosensitivity Index CI", British Journal of Haematology, vol. 128, No. 6, Mar. 1, 2005, pp. 783-791.
Dupree, Beth B., et al., "Breast biopsies obtained with MAM-MOTOME ((R)) device can be tested ex vivo with ChemoFx((R)) assay," Proceedings of the Annual Meeting of the American Association for Cancer Research, vol. 47, Apr. 1, 2006, p. 1285.
O'Shaughnessy, J.A., "Feasibility of testing core needle biopsies ex vivo in the ChemoFx assay," Journal of clinical Oncology, vol. 24, No. 18s, 20073, Jun. 2006, 2006 ASCO Meeting Proccedings, abstract.
"4.3 Statistische Methoden", In: Ravea Lube: "Individuelle Vorhersage des Chemoterapieansprechens mittles in-vitro Chemosensiblitatstestugn bei Patienten mit chronischer Lymphatisher Leukamie", Apr. 27, 2007, pp. 43-46.

(Continued)

*Primary Examiner* — Sean Aeder
(74) *Attorney, Agent, or Firm* — Cooley, LLP

(57) ABSTRACT

The present invention provides methods for individualizing chemotherapy, and particularly methods for individualizing neoadjuvant chemotherapy. The present invention provides methods for predicting a cancer patient's response to neoadjuvant chemotherapy, including assessing the probability of a positive response upon treatment with candidate agents prior to surgery. In various aspects, the invention involves culturing a monolayer of malignant cells from an explant of a patient's biopsy specimen, such as a transcutaneous biopsy-sized specimen, and testing the malignant cells for resistance or sensitivity to one or a plurality of candidate agents for neoadjuvant therapy. In other aspects, the invention provides methods for accurately scoring and interpreting such assays, and discloses in vitro chemoresponse results that are predictive of a patient's pathological complete response (pCR) upon receiving the corresponding treatment regimen.

18 Claims, 4 Drawing Sheets

OTHER PUBLICATIONS

Ochs, R.L., et al., "Phenotypic Cell Culture Assay for Predicting Anticancer Drug Responses," Preclinica, vol. 2, No. 3, May 1, 2004, pp. 205-212.

Supplementary European Search Report received in co-pending related European application No. EP 08 84 0503, mailed Nov. 9, 2010, 11 pages.

* cited by examiner

METHODS FOR SELECTING ACTIVE AGENTS FOR CANCER TREATMENT

This application claims priority to U.S. Provisional Application No. 60/980,098, filed Oct. 15, 2007, the entire disclosure of which is hereby incorporated by reference in its entirety.

BACKGROUND

Neoadjuvant chemotherapy refers to drug treatment administered to cancer patients prior to surgery. A goal of neoadjuvant chemotherapy is to reduce the size of the cancer before surgery, thus making surgery easier and more likely to be successful. Neoadjuvant chemotherapy is used commonly in cancers that are locally advanced and/or inoperable. The use of such chemotherapy can effectively reduce the difficulty and morbidity of a subsequent surgical procedure; for example in the case of breast cancer, allowing for breast-conserving surgery to be performed instead of mastectomy.

Neoadjuvant chemotherapy has improved overall survival rates in breast cancer patients from 10-20% by local therapy alone to 30-60% with neoadjuvant chemotherapy followed by local therapy (3). However, achieving maximal benefits of neoadjuvant chemotherapy depends on the selection of an effective chemotherapy regimen. The choice of regimen by the treating oncologist is typically based on clinical and histological features and historical population response rates and not individualized to that patient. As a result, many patients are treated with unnecessary or ineffective chemotherapy, which can result in unnecessary toxicity and costs, may delay more effective treatment, and may cause the tumor to become cross-resistant to additional drugs (4).

Inadequate treatment choices for neoadjuvant therapy are partly due to the lack of accurate predictors of response in individual patients. While numerous in vitro chemosensitivity and resistance assays (CSRAs) have emerged, the assays are often limited in their utility for assessing neoadjuvant treatment, due to, for example, technical difficulties, the need for large amounts of fresh tissue (1-2 g), limited consistency in producing results (often less than 50% of submitted specimens), and the lack of reproducibility and clinical utility in predicting patient outcomes (5, 6).

SUMMARY OF THE INVENTION

The present invention provides methods for individualizing chemotherapy, and particularly methods for individualizing neoadjuvant chemotherapy. The present invention provides methods for predicting a cancer patient's response to neoadjuvant chemotherapy, including assessing the probability of a positive response (e.g., pathological complete response (pCR)) upon treatment with candidate agents prior to surgery. In various aspects, the invention involves culturing a monolayer of malignant cells from an explant of a patient's biopsy specimen, such as a transcutaneous biopsy-sized specimen, and testing the malignant cells for resistance or sensitivity to one or a plurality of candidate agents for neoadjuvant therapy. In other aspects, the invention provides methods for accurately scoring and interpreting such assays, and discloses in vitro chemoresponse results that are predictive of a patient's pathological complete response (pCR) upon receiving the corresponding treatment regimen.

In one aspect, the invention provides a method for culturing malignant cells from transcutaneouos biopsy-sized specimens, so that a tumor's sensitivity or resistance to candidate agent(s) can be evaluated without surgery. Such specimens, such as breast tissue specimens, may be obtained, for example, via core needle biopsy or MAMMOTOME® biopsy system, and may contain 50 mg of tissue or less. The present invention allows malignant cells from such specimens to be reproducibly cultured for chemosensitivity and resistance testing, so that neoadjuvant chemotherapy may be selected on an individualized basis.

In a second aspect, the invention provides methods, including algorithms, for assessing the sensitivity of cells to active agents. The method involves determining a cytotoxic index within a dose range, and calculating an adjusted area under the curve (aAUC) for the resulting dose-response curve. The aAUC for an active agent accurately reflects the sensitivity of cells to in vitro drug exposure, and takes into account differences in dose/response curve shapes. Thus, according to this aspect, the invention provides algorithms for scoring the sensitivity of cultured cells to drugs, thereby allowing accurate evaluations of chemosensitivity/resistance. Such algorithms improve the interpretation of chemosensitivity data, to individualize chemotherapy selection, including neoadjuvant chemotherapy selection.

In a third aspect, the invention provides a method for predicting the effectiveness, for a given breast cancer patient, of various neoadjuvant chemotherapy regimens that are currently employed for the treatment of breast cancer. For example, the invention provides a method for predicting a patient's response to a neoadjuvant chemotherapy regimen comprising docetaxel/fluorouracil (DF), or related agents. As disclosed herein, in vitro sensitivity to DF or related agents is an independent predictor of a positive outcome (e.g., pCR) to a neoadjuvant chemotherapy regimen comprising DF. The invention thereby supports individualized chemotherapy decisions, including decisions involving treatment with DF or related agents, prior to surgery.

DETAILED DESCRIPTION OF THE INVENTION

Figure 1:
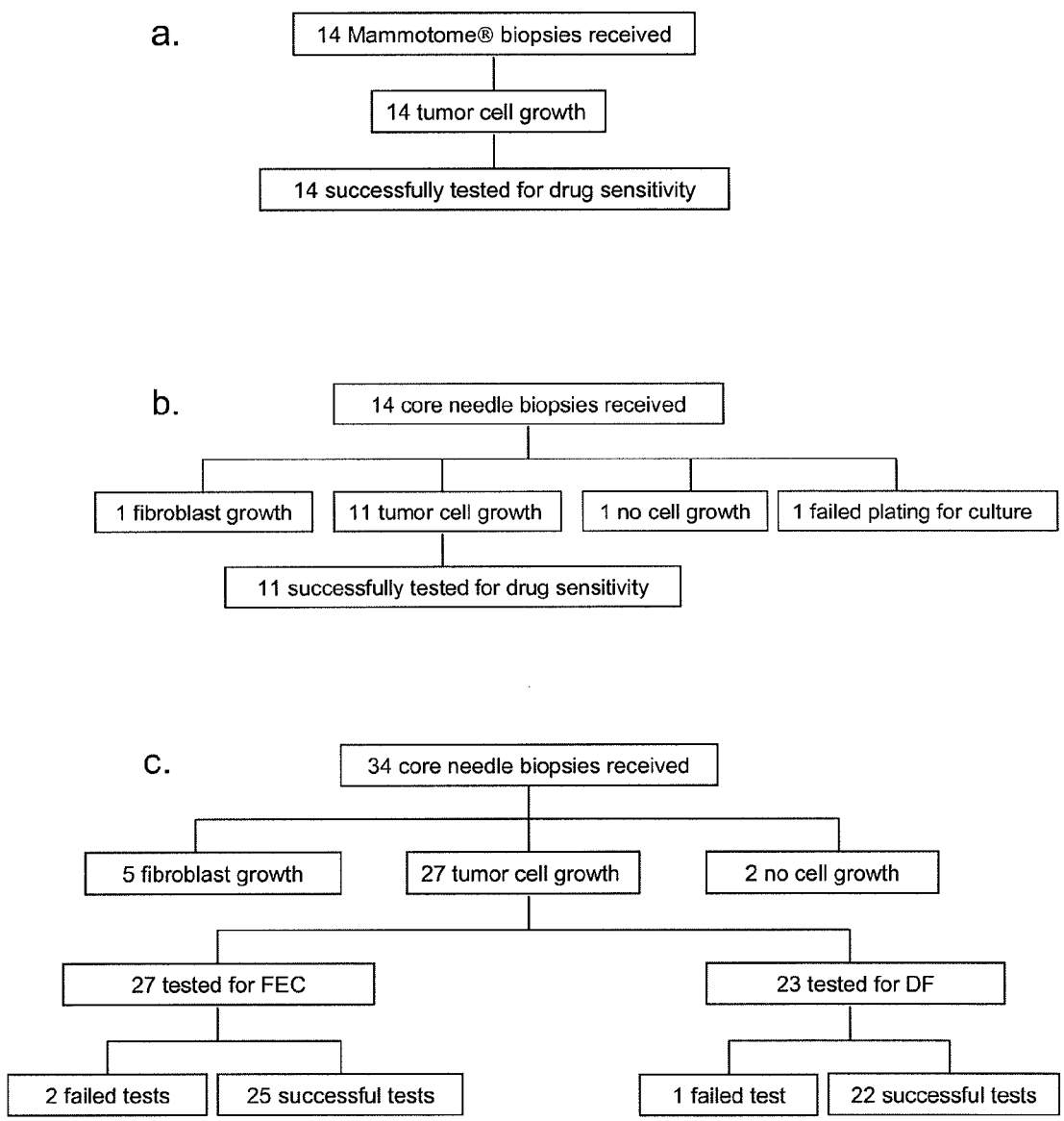
FIG. 1 is a flow chart depicting ChemoFx® assay accessibility. Cells from biopsy specimens were tested for chemosensitivity with the ChemoFx® assay. Panel a: MAMMOTOME®, 100% accessibility; Panel b: Core needle biopsies, 78.6% accessibility; Panel c: Core needle biopsies from a subset of patients from US Oncology 02-103 trial, 79.4% accessibility. The overall ChemoFx® assay accessibility for neoadjuvant breast cancer biopsies was 83.9%.

The present invention provides methods for individualizing chemotherapy, and particularly methods of individualizing neoadjuvant chemotherapy. The present invention provides methods for predicting a cancer patient's response to neoadjuvant chemotherapy, including methods for scoring assays and methods for assessing the probability of a positive response (e.g., a pathological complete response (pCR)) upon treatment with candidate agents prior to surgery.

In various aspects, the invention involves culturing a monolayer of malignant cells from an explant of a patient's biopsy specimen, such as a transcutaneous biopsy-sized specimen, and testing the malignant cells for resistance or sensitivity to one or a plurality of candidate agents for neoadjuvant therapy. In other aspects, the invention provides methods for accurately scoring such assays, for example, by determining a cytotoxic index within a dose range, and calculating an adjusted area under the curve (aAUC) for the resulting dose-response curve. Such algorithms accurately reflect the sensitivity of cells to in vitro drug exposure. In still other aspects, the invention provides predictors of pCR, including in vitro tumor sensitivity to docetaxel/fluorouracil exposure. As disclosed herein, in vitro sensitivity to DF is an independent predictor of pCR for breast cancer patients upon treatment with a regimen comprising DF.

Patients and Specimens

The present invention supports individualized chemotherapy decisions for cancer patients. The present invention provides chemoresponse/resistance assays requiring only small amounts of malignant tissue, and provides methods of scoring such assays' for accurately assessing the level of chemosensitivity. In various embodiments, the cancer patient may have a cancer selected from breast, ovarian, colorectal, endometrial, thyroid, nasopharynx, prostate, head and neck, liver, kidney, pancreas, bladder, brain, and lung. In certain embodiments, the tumor is a solid tissue tumor and/or is epithelial in nature. For example, the patient may be a breast cancer patient.

In certain aspects of the invention, the patient is a candidate for neoadjuvant chemotherapy, that is, the patient has not had surgery to remove cancerous tissue, but will receive chemotherapy to shrink and/or downgrade the tumor prior to any surgery. Thus, as used herein, the term "neoadjuvant chemotherapy" means chemotherapy administered to cancer patients prior to surgery. Types of cancers for which neoadjuvant chemotherapy is commonly considered include, for example, breast, colorectal, ovarian, cervical, bladder, and lung. In certain embodiments, the patient is a breast cancer patient that will receive neoadjuvant chemotherapy.

In certain embodiments, the present invention provides chemoresponse/resistance assays for predicting a patients response to a neoadjuvant chemotherapy. In such embodiments, the tumor specimen is a transcutaneous biopsy-sized specimen, and generally contains less than 100 mg of tissue, or in certain embodiments, contains 50 mg of tissue or less. The tumor specimen (or biopsy) may contain from about 20 mg to about 50 mgs of tissue, such as about 35 mg of tissue. The tissue may be obtained, for example, as one or more (e.g., 1, 2, 3, 4, or 5) core needle biopsies (e.g., using a 14-gauge needle or other suitable size). In other embodiments, the sample may be obtained via a device such as the MAMMO-TOME® biopsy system, which is a laser guided, vacuum-assisted biopsy system for breast biopsy.

Chemoresponse Assay

The present invention involves conducting chemoresponse testing with one or a panel of chemotherapeutic agents on cultured cells from a cancer patient. In certain embodiments, the chemoresponse method is as described in U.S. Pat. Nos. 5,728,541, 6,900,027, 6,887,680, 6,933,129, 6,416,967, 7,112,415, and 7,314,731 (all of which are hereby incorporated by reference in their entireties). The chemoresponse method may further employ the variations described in US Published Patent Application Nos. 2007/0059821 and 2008/0085519, both of which are hereby incorporated by reference in their entireties. Such chemoresponse methods are commercially available as the ChemoFx® Assay (Precision Therapeutics, Inc, Pittsburgh, Pa.).

Briefly, in certain embodiments, cohesive multicellular particulates (explants) are prepared from a patient's tissue sample (e.g., a biopsy sample) using mechanical fragmentation. This mechanical fragmentation of the explant may take place in a medium substantially free of enzymes that are capable of digesting the explant. However, in some embodiments, some enzymatic treatment may be conducted. Generally, the tissue sample is systematically minced using two sterile scalpels in a scissor-like motion, or mechanically equivalent manual or automated opposing incisor blades. This cross-cutting motion creates smooth cut edges on the resulting tissue multicellular particulates. The tumor particulates each measure from about 0.25 to about 1.5 $mm^3$, for example, about 1 $mm^3$.

After the tissue sample has been minced, the particles are plated in culture flasks (e.g., about 5 to 25 explants per flask). For example, about 9 explants may be plated per T-25 flask, or about 20 particulates may be plated per T-75 flask. For purposes of illustration, the explants may be evenly distributed across the bottom surface of the flask, followed by initial inversion for about 10-15 minutes. The flask may then be placed in a non-inverted position in a 37° C. $CO_2$ incubator for about 5-10 minutes. Flasks are checked regularly for growth and contamination. Over a period of a few weeks a cell monolayer will form. Further, it is believed (without any intention of being bound by the theory) that tumor cells grow out from the multicellular explant prior to stromal cells. Thus, by initially maintaining the tissue cells within the explant and removing the explant at a predetermined time (e.g., at about 10 to about 50 percent confluency, or at about 15 to about 25 percent confluency), growth of the tumor cells (as opposed to stromal cells) into a monolayer is facilitated. Further, in certain embodiments, the tumor explant may be agitated to substantially release tumor cells from the tumor explant, and the released cells cultured to produce a cell culture monolayer. The use of this procedure to form a cell culture monolayer helps maximize the growth of representative tumor cells from the tissue sample.

Prior to the chemotherapy assay, the growth of the cells may be monitored, and data from periodic counting may be used to determine growth rates which may or may not be considered parallel to growth rates of the same cells in vivo in the patient. If growth rate cycles can be documented, for example, then dosing of certain active agents can be customized for the patient. Monolayer growth rate may be monitored using, for example, a phase-contrast inverted microscope. Generally, the monolayers are monitored to ensure that the cells are actively growing at the time the cells are suspended for drug exposure. Thus, the monolayers will be non-confluent when the cells are suspended for chemoresponse testing.

A panel of active agents may then be screened using the cultured cells. Generally, the agents are tested against the cultured cells using plates such as microtiter plates. For the chemosensitivity assay, a reproducible number of cells is delivered to a plurality of wells on one or more plates, preferably with an even distribution of cells throughout the wells. For example, cell suspensions are generally formed from the monolayer cells before substantial phenotypic drift of the tumor cell population occurs. The cell suspensions may be, without limitation, about 4,000 to 12,000 cells/ml, or may be about 4,000 to 9,000 cells/ml, or about 7,000 to 9,000 cells/ml. The individual wells for chemoresponse testing are inoculated with the cell suspension, with each well or "segregated site" containing about $10^2$ to $10^4$ cells. The cells are generally cultured in the segregated sites for about 4 to about 30 hours prior to contact with an agent.

Each test well is then contacted with at least one pharmaceutical agent, or a sequence of agents. The panel of chemotherapeutic agents may comprise at least one agent selected from a platinum-based drug, a taxane, a nitrogen mustard, a kinase inhibitor, a pyrimidine analog, a podophyllotoxin, an anthracycline, a monoclonal antibody, and a topoisomerase I inhibitor. For example, the panel may comprise 1, 2, 3, 4, or 5 agents selected from bevacizumab, capecitabine, carboplatin, cecetuximab, cisplatin, cyclophosphamide, docetaxel, doxorubicin, epirubicin, erlotinib, etoposide, 5-fluorouracil, gefitinib, gemcitabine, irinotecan, oxaliplatin, paclitaxel, panitumumab, tamoxifen, topotecan, and trastuzumab, in addition to other potential agents for treatment. In certain embodiments, the chemoresponse testing includes one or more combination treatments, such combination treatments including one or more agents described above. Generally, each agent in the panel is tested in the chemoresponse assay at a plurality of concentrations representing a range of expected extracellular fluid concentrations upon therapy.

In certain embodiment, the patient's cultured cells are tested for a level of sensitivity/resistance against 1, 2, 3, 4, or 5 of the following agents or combinations thereof:

| Drug | Also known as . . . |
|---|---|
| Altretamine | Hexalen ®, hydroxymethylpentamethylmelamine (HMPMM) |
| Bleomycin | Blenoxane ® |
| Carboplatin | Paraplatin ® |
| Carmustine | BCNU, BiCNU ® |
| Cisplatin | Platinol ®, CDDP |
| Cyclophosphamide | Cytoxan ®, Neosar ®, 4-hydroperoxycyclophosphamide, 4-HC |
| Docetaxel | Taxotere ®, D-Tax |
| Doxorubicin | Adriamycin ®, Rubex ®, Doxil ®* |
| Epirubicin | Ellence ® |
| Erlotinib | Tarceva ®, OSI-774 |
| Etoposide | VePesid ®, Etopophos ®, VP-16 |
| Fluorouracil | Adrucil ®, 5-FU, Efudex ®, Fluoroplex ®, Capecitabine*, Xeloda ®* |
| Gemcitabine | Gemzar ® |
| Ifosfamide | Ifex ®, 4-hydroperoxyifosfamide, 4-HI |
| Irinotecan/SN-38 | Camptosar ®, CPT-11, SN-38 |
| Leucovorin | Wellcovorin ® |
| Lomustine | CCNU, CeeNU ® |
| Melphalan | Alkeran ®, L-PAM |
| Mitomycin | Mutamycin ®, Mitozytrex ®, Mitomycin-C |
| Oxaliplatin | Eloxatin ® |
| Paclitaxel | Taxol ®, Abraxane ®* |
| Procarbazine | Matulane ®, PCZ |
| Temozolomide | Temodar ® |
| Topotecan | Hycamtin ® |
| Vinblastine | Velban ®, Exal ®, Velbe ®, Velsar ®, VLB |
| Vincristine | Oncovin ®, Vincasar PFS ®, VCR |
| Vinorelbine | Navelbine ®, NVB |

The efficacy of each agent in the panel is determined against the patient's cultured cells, by determining the viability of the cells (e.g., number of viable cells). For example, at predetermined intervals before, simultaneously with, or beginning immediately after, contact with each agent or combination, an automated cell imaging system may take images of the cells using one or more of visible light, UV light and fluorescent light. Alternatively, the cells may be imaged after about 25 to about 200 hours of contact with each treatment. The cells may be imaged once or multiple times, prior to or during contact with each treatment. Of course, any method for determining the viability of the cells may be used to assess the efficacy of each treatment in vitro.

In certain embodiments, the patient's cells show a heterogeneous response across the panel of agents and/or combination, making the selection of an agent particularly crucial for the patient's treatment.

Algorithms

The output of the assay is a series of dose-response curves for tumor cell survivals under the pressure of a single or combination of drugs, with multiple dose settings each (e.g., ten dose settings). To better quantify the assay results, the invention provides a scoring algorithm accommodating a dose-response curve. Specifically, the invention in certain aspects provides an algorithm to quantify chemoresponse assay results by determining an adjusted area under curve (aAUC).

However, since a dose-response curve only reflects the cell survival pattern in the presence of a certain tested drug, assays for different drugs and/or different cell types have their own specific cell survival pattern. Thus, dose response curves that share the same aAUC value may represent different drug effects on cell survival. Additional information may therefore be incorporated into the scoring of the assay. In particular, a factor or variable for a particular drug or drug class (such as those drugs and drug classes described) and/or reference scores may be incorporated into the algorithm.

Figure 4:
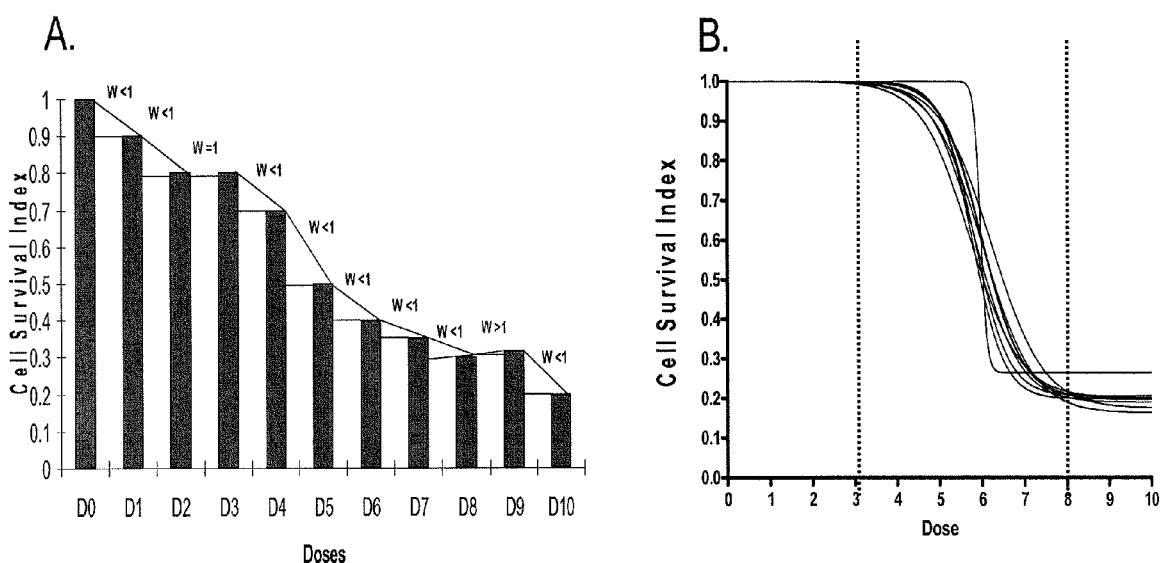
FIG. 4 illustrates the relationship between a dose response curve and aAUC. Panel A shows different local slopes at different dose points. Local slope may be determined by $S_d=(CI_d-CI_{d-1})$/Unit of Dose. As shown, there is a zero slope between dose 2 and dose 3, which may be given a weight equal to 1, and there is a negative slope between dose 8 and dose 9, which may be given a weight larger than one. The majority of local slopes are positive, and may be given weights less than one. The smaller weight means a steep slope, and indicates a more effective dose or a drug. Panel B shows that the major variation of the dose response curve is in the middle dose ranges, which provides a rational for curve truncation in determining aAUC.

For example, in certain embodiments, the invention quantifies and/or compares the in vitro sensitivity/resistance of cells to drugs having varying mechanisms of action, and thus, in some cases, different dose-response curve shapes. Exemplary drugs and drug classes are described herein. In these or other embodiments, the invention compares the sensitivity of the patient's cultured cells to a plurality of agents that show some effect on the patient's cells in vitro (e.g., all score sensitive to some degree), so that the most effective agent may be selected for therapy. In such embodiments, an aAUC is calculated to take into account the shape of a dose response curve for any particular drug or drug class. The aAUC takes into account changes in cytotoxicity between dose points along a dose-response curve, and assigns weights relative to the degree of changes in cytotoxicity between dose points. For example, changes in cytotoxicity between dose points along a dose-response curve may be quantified by a local slope, and the local slopes weighted along the dose-response curve to emphasize cytotoxicity. See FIG. 4A.

For example, aAUC may be calculated as follows.

Step 1: Calculate Cytotoxity Index (CI) for each dose, where $CI=Mean_{drug}/Mean_{control}$.

Step 2: Calculate local slope ($S_d$) at each dose point, for example, as $S_d=(CI_d-CI_{d-1})/Unit\ of\ Dose$, or $S_d=(CI_{d-1}-CI_d)/Unit\ of\ Dose$.

Step 3: Calculate a slope weight at each dose point, e.g., $W_d=1-S_d$.

Step 4: Compute aAUC, where $aAUC=\Sigma\ W_d\ CI_d$, and where, $d=1, 2, \ldots, 10$; $aAUC \sim (0, 10)$; And at $d=1$, then $CI_{d-1}=1$. Equation 4 is the summary metric of a dose response curve and may used for subsequent regression over reference outcomes.

Usually, the dose-response curves vary dramatically around middle doses, not in lower or higher dose ranges. See FIG. 4B. Thus, the algorithm in some embodiments need only determine the aAUC for a middle dose range, such as for example (where from 8 to 12 doses are experimentally determined, e.g., 10 doses), the middle 4, 5, 6, or 8 doses are used to calculate aAUC. In this manner, a truncated dose-response curve might be more informative in outcome prediction by eliminating background noise.

The numerical aAUC value (e.g., test value) may then be evaluated for its effect on the patient's cells, and compared to the same metric for other drugs on the patient's cells. For example, a plurality of drugs may be tested, and aAUC determined as above for each, to determine whether the patient's cells have a sensitive response, intermediate response, or resistant response to each drug. Further, the measures may be compared to determine the most effective drug.

In some embodiments, each drug is designated as, for example, sensitive, or resistant, or intermediate, by comparing the aAUC test value to one or more cut-off values for the particular drug (e.g., representing sensitive, resistant, and/or intermediate aAUC scores, or aAUC for that drug). The cut-off values for any particular drug may be set or determined in a variety of ways, for example, by determining the distribution of a clinical outcome (as described and exemplified herein) within a range of corresponding aAUC reference scores. That is, a number of patient tumor specimens are tested for chemosenstivity/resistance (as described herein) to a particular drug prior to treatment, and aAUC quantified for each specimen. Then after clinical treatment with that drug, aAUC values that correspond to a clinical response (e.g., sensitive) and the absence of significant clinical response (e.g., resistant) are determined. Cut-off values may alternatively be determined from population response rates. For example, where a patient population is known to have a response rate of 30% for the tested drug, the cut-off values may be determined by assigning the top 30% of aAUC scores for that drug as sensitive. Further still, cut-off values may be determined by statistical measures, such as mean or median scores.

In other embodiments, the aAUC scores may be a continuous scale. For example, aAUC values for dose response curves were regressed over a reference scoring algorithm which was adjusted for test drugs. The reference scoring algorithm provided a three ordinal categorical outcome— sensitive (s), intermediate sensitive (i) and resistant (r). Logistic regression was used to incorporate the different information, i.e., three outcome categories, into the scoring algorithm. However, regression can be extended to other forms, such as linear or generalized linear regression, depending on reference outcomes. The regression model was fitted as the following: Logit (Pref)=$\alpha=\beta$ (aAUC)+$\gamma$ (drugs), where $\gamma$ is a covariate vector and the vector can be extended to clinical and genomic features. The score was calculated as Score=$\beta$ (aAUC)+$\gamma$ (drugs). Since the score is a continuous variable, results may be classified into clinically relevant categories, i.e., sensitive (S), intermediate sensitive (I), and resistant (R), based on the distribution of a reference scoring category or maximized sensitivity and specificity relative to the reference.

Prognostic Predictors

In certain aspects, the invention provides predictors of a positive response to neoadjuvant chemotherapy, including neoadjuvant chemotherapy for breast cancer. The response may be a complete response, and which may be an objective response, a clinical response, or a pathological response to treatment. For example, the response may be determined based upon the techniques for evaluating response to treatment of solid tumors as described in Therasse et al., *New Guidelines to Evaluate the Response to Treatment in Solid Tumors, J. of the National Cancer Institute* 92(3):205-207 (2000), which is hereby incorporated by reference in its entirety. The response may be a duration of survival (or probability of such duration) or progression-free interval. The timing or duration of such events may be determined from about the time of diagnosis or from about the time treatment (e.g., chemotherapy) is initiated. Alternatively, the response may be based upon a reduction in tumor size, tumor volume, or tumor metabolism, or based upon overall tumor burden, or based upon levels of serum markers especially where elevated in the disease state.

The response in individual patients may be characterized as a complete response, a partial response, stable disease, and progressive disease, as these terms are understood in the art. In certain embodiments, the response is a pathological complete response. A pathological complete response, e.g., as determined by a pathologist following examination of tissue (e.g., breast or nodes in the case of breast cancer) removed at the time of surgery or biopsy, generally refers to an absence of histological evidence of invasive tumor cells in the surgical specimen.

The probability of positive response to neoadjuvant therapy, including a complete response, may be determined by testing for the sensitivity of the patient's cultured cells to docetaxel/fluorouracil (DF), for example, as described herein. Sensitivity to DF in a chemoresponse test, as disclosed herein, is an independent predictor of a pathological complete response, upon treatment with DF. In certain embodiments, the sensitivity to DF is quantified by an aAUC for DF.

Additional predictors of response, which may be independent of DF sensitivity, include cancer stage, grade, estrogen receptor, PR and Her2. Such markers may be combined in accordance with the invention to add additional predictive value.

EXAMPLES

Summary

Transcutaneous sampling of breast lesions was accomplished in two small feasibility studies of the MAMMO-TOME® (n=14) and a routine core needle biopsy (n=14). In addition, 34 patients with node-positive breast cancer in the US Oncology 02-103 trial were analyzed. One to three cores from each tumor before treatment were received. In addition, on the samples received from the US Oncology 02-103 trial, the expanded tumor cells were tested for chemoresponse using a cell-based assay and scored as adjusted area under the curve (aAUC). Assay score and pathological complete response (pCR) were determined independently and in a blinded manner. Logistic regression models were fitted to select predictors for responsiveness.

Tumor cells were successfully isolated from 83.9% of the patients. The chemoresponse profiles of the subset of patients were robust and reproducible with coefficient of variance of less than 3%. In the initial outcome correlation, aAUC of docetaxel/fluorouracil (DF) was a significant predictor of pCR; the accuracy of the cross-validated model was 75%.

Material and Methods

To determine the feasibility of chemoresponse assay testing in tumor cells cultured from patient biopsies using the ChemoFx® assay, 14 specimens obtained via the MAMMO-TOME® Breast Biopsy System and 14 specimens obtained from core needle biopsies, were tested. All were specimens supplied by collaborating physicians. The MAMMO-TOME® Breast Biopsy System is an ultrasound guided, vacuum assisted biopsy device using an 11-gauge probe to extract tissue (estimated yield approximately 100 mg) (9, 10). With respect to core needle biopsy, one to four core needle biopsy specimens per patient were collected using a 14-gauge needle (estimated per patient yield 15 to 50 mg) (10). A primary culture of each specimen was established and the in vitro chemoresponse profiles of each culture were evaluated. The drugs tested on the MAMMOTOME® specimens were cyclophosphamide, docetaxel, doxorubicin, 5-fluorouracil, gemcitabine, irinotecan, methotrexate, and paclitaxel, and on the needle biopsy specimens capecitabine, cisplatin, cyclophosphamide, docetaxel, doxorubicin, epirubicin, etoposide, 5-fluorouracil, gemcitabine, irinotecan, paclitaxel, and vinorelbine. Success was defined as the ability to grow enough cells to test at least 2 chemotherapy drugs per specimen using the ChemoFx® assay (Precision Therapeutics, Pittsburgh, Pa.)

Tissue specimens were obtained from the last 34 patients enrolled in the US Oncology 02-103 trial. Inclusion and exclusion criteria were those of the original trial. As part of the US Oncology trial, each patient was treated with neoadjuvant chemotherapy consisting of four cycles of fluorouracil/epirubicin/cyclophosphamide (FEC) followed by four cycles of docetaxel/fluorouracil (DF). Patients positive for human epidermal growth factor receptor 2 (Her2) status also received Herceptin, a Her2 inhibitor. All patients provided written informed consent and the study was approved by the Institutional Review Boards of the participating US Oncology 02-103 study sites.

At the time of all biopsies, each tissue sample was placed in the supplied 125 mL bottle containing sterile McCoy's shipping media (Mediatech, Herndon, Va.) and shipped overnight to Precision Therapeutics, Inc. (PTI) laboratories in Pittsburgh, Pa.

Clinical Utility of ChemoFx® Assay for Breast Cancer

To assess the feasibility of the ChemoFx® assay in predicting the clinical outcome of breast cancer patients, the assay was used to test the cells obtained from core biopsies of the 34 patients enrolled in the US Oncology 02-103 trial for their responsiveness to FEC and DF. Three main outcomes were evaluated: drug responsiveness, clinical endpoint, and clinical prognostic factors. As part of the ongoing US Oncology trial, the clinical endpoint pathological complete response (pCR) and the clinical prognostic factors estrogen receptor (ER), progesterone receptor (PR), and Her2 status, as well as tumor stage and histological grade were recorded and evaluated. ChemoFx® assay results and pCR were determined independently and in a blinded manner.

ChemoFx® Assay

Upon arrival in the laboratory, the biopsies were minced into small pieces and placed in mammary epithelial growth medium (MEGM, Lonza, Walkersville, Md.). Over time, cells migrated out of the tumor pieces to form a monolayer on the bottom of the flask. Once sufficient cells had grown out of the in vitro explants, they were trypsinized and reseeded into microtiter plates for both the ChemoFx® assay and for immunohistochemsitry (IHC) analysis to confirm epithelial cell growth. Only cultures demonstrating greater than 65% epithelial cells were considered for testing. For the ChemoFx® assay, a cell suspension was prepared from the cell monolayer and was delivered to a large basin situated on the stage of the Oasis LM liquid handling machine (Dynamic Devices, Inc., Newark, Del.). The liquid handler then seeded a set number of cells into the wells of a 384-well microtiter plate in replicates of three per dose per drug treatment. Cells were then allowed to adhere to the plate and grow for 24 hours at 37° C. Following this incubation, the liquid handler prepared ten doses of each drug or drug combination in the appropriate growth medium via serial dilutions. The appropriate volume of each dose of each drug or drug combination was then added to the corresponding well of cells in the 384-well plate via the liquid handler; each drug treatment also contained three control wells to which medium alone was added. The software ensures that the liquid handler treats all cells with the correct drug or drug combination at the correct dosage. The cells were incubated with drugs for 72 hours. Subsequently, the liquid handler removed media and any nonadherent, dead cells from each well. The remaining cells were then fixed in 95% ethanol containing the DNA intercalating blue fluorescent dye, 4',6-diamidino-2-phenylindole dihydrochloride (DAPI) (Molecular Probes, Eugene, Oreg.). Following fixation and staining, an automated microscope captured UV images of the stained cells in each well. The number of cells per well, in both visible and UV light, was then quantified. For each dose of each drug treatment tested, a cytotoxic index (CI) was calculated according to the formula, $CI = Mean_{drug}/Mean_{control}$, which represents the ratio of cells killed as a result of the treatment.

As the clinical formulations of cyclophosphamide, capecitabine, and irinotecan are inert in vitro, the active metabolites were used in the assay system for these drugs (4-hydroperoxycyclophosphamide, 5-fluorouracil, and SN-38, respectively).

aAUC Computation

The area under the dose response curve (AUC) represents the fraction survival of cells in the presence of drug at each of the 10 increasing dose concentrations. There can be certain circumstances when dose response curves of differing shapes share similar AUCs. Therefore, as a better reflection of sensitivity to drug treatment, an adjusted area under the curve (aAUC) was calculated according to the following formulas. First, local slope ($S_d$) at each dose point was calculated based on $S_d = (CI_{d-1} - CI_d)/$Unit of Dose. Second, slope weight at each dose point was calculated based on $W_d = 1 - S_d$. Finally, aAUC was computed based on $aAUC = \Sigma W_d \, CI_d$, where, $d = 1, \ldots 10$. To capture important assay information, an aAUC was computed based on a truncated dose response curve from dose three to dose seven and used as the assay metric for data analyses.

Analytical Reproducibility of the ChemoFX® Assay

To demonstrate the reproducibility of the ChemoFx® Assay, replicate runs of FEC and DF were performed. Briefly, nine separate plates were prepared using HTB77 cell lines (ATCC, Manassas, Va.). The FEC and DF drug combinations were prepared in the appropriate concentrations to mimic the conditions of primary tumor samples in the ChemoFx® assay and the resulting aAUC was calculated per treatment. The coefficient of variance of the calculated aAUC was determined for FEC and DF treatments across the nine plates.

Data Analyses

Data analyses were performed using SAS 8.1 (SAS Institute, Cary, N.C.) and R 2.5.0, (free software downloaded from r-project.org). The three types of variables involved in the data analyses represented the three study outcomes: ChemoFx® assay metrics (aAUCs) as a measure of drug responsiveness, the clinical endpoint (pCR), and the clinical prognostic factors (stage, grade, and ER, PR and Her2 status). The assay metric aAUC was dichotomized as resistant (R): greater than 3.1 for FEC curves and greater than 4.1 for DF curves or sensitive (S): less than or equal to 3.1 for FEC curves and less than or equal to 4.1 for DF curves. These cut-off points were based on the patient cohort pCR distribution. pCR was coded as 1 for pathological complete response and 0 for non-pathological complete response at the end of the chemotherapy. For clinical prognostic factors, ER, PR, and Her2 were coded as 1 if positive and 0 if negative, whereas, stage III and grade G3 were coded as 1 and stage II and grade G2 were coded as 0. The clinical endpoint pCR was considered as a dependent variable to fit logistic regression models. aAUC of FEC dose response curves (aAUC_FEC) and aAUC of DF dose response curves (AUC_DF) were fitted in the models as predictors. The correlations between pCR and the clinical factors or the assay metrics were evaluated by 2×2 tables, and the statistical significance was obtained by Fisher exact tests. Permutation and Bootstrap techniques were used to verify the significance levels. The stepwise approach was used for model selection when clinical factors were included in the model selection, and the model fitting was cross-validated using the leave one out cross validation (LOOCV) technique. The model accuracy was then calculated by (true positive+true negative)/total sample.

Results

All MAMMOTOME® specimens were successfully cultured and all specimens were tested for chemoresponsiveness with the ChemoFx® assay (FIG. 1A). The average number of drugs tested per specimen was 10.9 (range: 6-18). Of the 14 specimens obtained by core biopsy, 11 (78.6%) grew successfully and 11 were tested for chemoresponsiveness with the ChemoFx® assay (FIG. 1B). The average number of drugs tested for each biopsy specimen was 6.7 (range: 1-12). Of the 34 core needle biopsies received from the US Oncology 02-103 patients, tumor cells were successfully isolated and expanded from 27 of them, yielding a success rate of 79.4% (FIG. 1C). Overall, tumor cell growth and testing were successful and were tested in 83.9% of the patient specimens.

Figure 2:
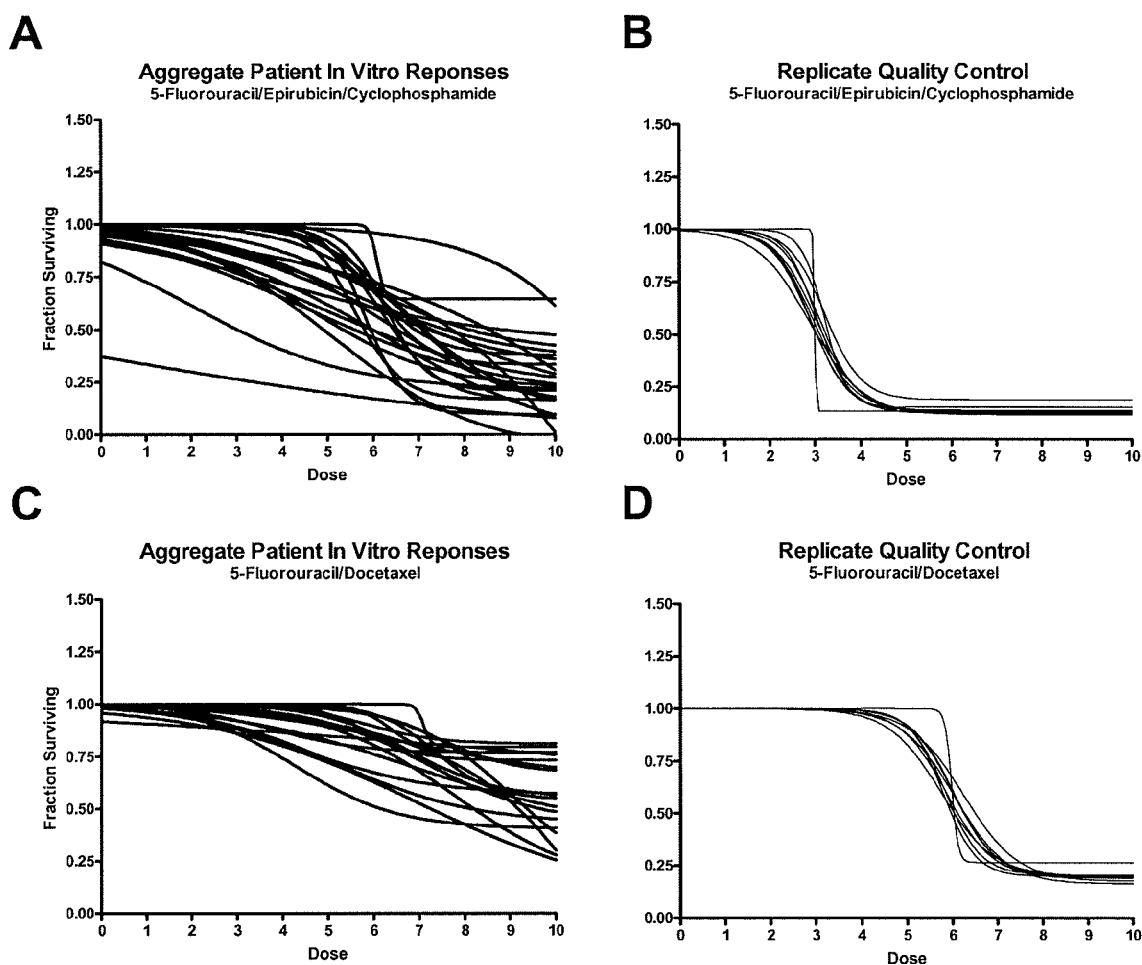
FIG. 2 shows in vitro responses of neoadjuvant breast cancer patient primary cultured cells tested for fluorouracil/epirubicin/cyclophosphamide (FEC) and docetaxel/capecitabine (TX) compared with that of HTB 77 breast cancer line from ATCC. Panel A: patient primary cultured cells from US Oncology 02-103 trial tested for FEC chemosensitivity; Panel B: HTB77 cells tested for FEC chemosensitivity; Panel C: patient primary cultured cells from US Oncology 02-103 trial tested for TX chemosensitivity; Panel D: replicate HTB77 cells tested for TX chemosensitivity. Dose-response curves from multiple HTB77 cell line tests were clustered together with small coefficients of variability, whereas, dose-response curves across individual patient's primary cultured cells demonstrated more heterogeneity of in vitro response. Dose units shown on the X axes are the serial drug dilutions, not the actual drug dose.

FIG. 2 shows the in vitro patient tumor cell responses to FEC and DF as well as the replicate quality control plate results. Across the nine replicates, the coefficients of variation (COV) were 2.9% and 2.3% for DF and FEC, respectively. COVs for the patient in vitro responses were nearly 3 and 5 times larger (8% and 11%) for DF and FEC, respectively, indicating that the large variability of the dose-response curves across patients (FIGS. 2A and 2C) is due to interpatient variability in responses to DF and FEC, not to laboratory/assay-process variability (FIGS. 2B and 2D).

Figure 3:
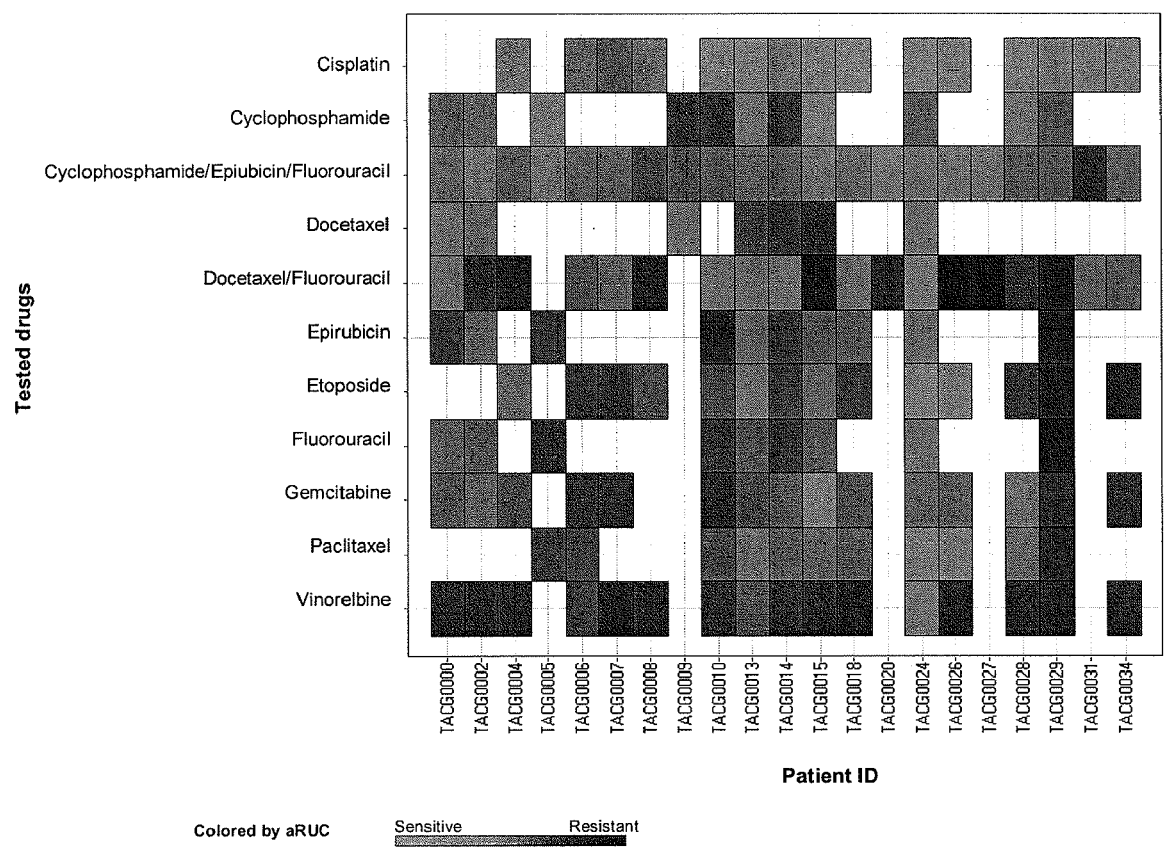
FIG. 3 illustrates the chemosensitivity heterogeneity among 22 patient biopsies from the US Oncology 02-103 trial tested by the ChemoFx® assay. Eleven chemotherapy regimens were tested. The heat map was generated from adjusted area under each dose response curve. Response is depicted over a spectrum from sensitive (light-colored boxes) to resistant (dark-colored boxes).

To determine the pattern of response to different drugs, the degree of assay response to each drug tested was plotted for the individual tumors as a heat map (FIG. 3). As can be seen from the distribution of responses, in vitro sensitivity or resistance to different drug regimens is highly patient specific. These results indicate that many of the patients had alternative therapies likely to be effective when the prescribed therapy was indicated as resistant.

The distribution of the available clinical factors of the 34 patients from the US Oncology 02-103 trial is listed in Table 1. Thirty-one of the 34 patients enrolled in the study had pCR determined. Of these, 13 achieved pCR yielding a response rate 41.9%. Among the 33 patients in which Her2 status was available, 23 were found to be Her2 positive.

TABLE I

Distribution of patient clinical features

| Clinical features | Status | n (%) |
|---|---|---|
| pCR (n = 31) | + | 13 (41.9) |
|  | − | 18 (58.0) |
| Stage (n = 32) | II | 22 (68.8) |
|  | III | 10 (31.2) |
| Grade (n = 30) | G2 | 8 (26.7) |
|  | G3 | 22 (73.3) |
| ER (n = 33) | + | 12 (6.4) |
|  | − | 21 (63.6) |
| PR (n = 34) | + | 12 (35.3) |
|  | − | 22 (64.7) |
| Her2 (n = 33) | + | 23 (69.7) |
|  | − | 10 (30.3) |

Clinical factors, such as stage, grade, ER status, PR status, and Her2 status are generally considered as prognostic factors associated with pCR. To evaluate the relationship between these clinical factors as well as the assay metrics (aAUC_FEC and aAUC_DF) with pCR, the data was analyzed by the two-sided Fisher exact test (Table 2). Although a higher percentage of samples from patients achieving pCR were Stage III, Grade G2, ER negative, PR negative, or Her2 positive status, none of these associations was statistically significant and therefore unlikely to affect the relationship between pCR and assay metrics. Of the two assay metrics (aAUC_FEC and aAUC_DF), only aAUC_DF sensitive status was significantly associated with pCR.

TABLE II

Relationship between pCR and clinical prognostic factors and ChemoFx ® assay metrics

|  |  | n | pCR (%) | P* |
|---|---|---|---|---|
| Stage | II | 20 | 8 (40.0) |  |
|  | III | 9 | 4 (44.4) | 1.00 |
| Grade | G2 | 8 | 5 (62.5) |  |
|  | G3 | 19 | 7 (36.8) | 0.40 |
| ER | + | 12 | 4 (33.3) |  |
|  | − | 19 | 9 (47.4) | 0.48 |
| PR | + | 11 | 4 (36.4) |  |
|  | − | 20 | 9 (45.0) | 0.72 |
| Her2 | + | 22 | 9 (40.9) |  |
|  | − | 8 | 3 (37.5) | 1.00 |
| aAUC_FEC | R | 15 | 6 (40.0) |  |
|  | S | 8 | 4 (50.0) | 0.68 |
| aAUC_DF | R | 14 | 4 (28.6) |  |
|  | S | 6 | 5 (83.3) | 0.05 |

*Two-sided Fisher exact test

The associations between pCR and the assay metrics were evaluated. By univariate logistic regression, aAUC_DF emerged as an independent variable (p=0.0425), with an odds ratio (OR) of 12.5 (Table 3A). These results were also verified by permutation and bootstrap procedures (data not shown). Subsequently, 2 types of multiple logistic regression models were fitted by a stepwise model selection approach. Model 1 was fitted with the assay variables and Model 2 was fitted with the assay variables together with the clinical factors. The inclusion of clinical factors had little effect on the association between aAUC_DF and pCR (Table 3A). Both models were essentially similar in being predictive as determined by LOOCV, each having cross-validated accuracies of 75% (Table 3B). However, the Model 2 fitting was less adequate than Model 1 due to limited sample size. Model 1 yielded a true positive accuracy of 83.3% and a true negative accuracy of 71.4%, corresponding to patients who tested sensitive to DF by this assay were nearly 3 times more likely to achieve pCR than those who tested resistant to DF (83.3% vs 28.6%).

TABLE IIIa

Associations between pCR and assay metrics

| Input variables | Selected variables | β | P | OR |
|---|---|---|---|---|
| Univariate logistic regressions | | | | |
| aAUC_FEC | | 0.40 | 0.65 | 1.50 |
| aAUC_DF | aAUC_DF | 2.53 | 0.04 | 12.50 |
| Multivariate logistic regressions (Stepwise model selection) | | | | |
| Model 1 | | | | |
| aAUC_FEC + aAUC_DF | | 2.53 | 0.04 | 12.50 |
| Model 2 | | | | |
| aAUC_FEC + aAUC_DF + Grade + Stage + ER + PR + Her2 | aAUC_DF | 2.37 | 0.07 | 10.67 |

TABLE IIIb

Predicted accuracies based on multiple logistic regressions by LOOCV

| | Observed (Model 1) | | | Observed (Model 2) | | |
|---|---|---|---|---|---|---|
| Predicted | pCR | non-pCR | Total | pCR | non-pCR | Total |
| pCR | 5 | 1 | 6 | 4 | 1 | 5 |
| non-pCR | 4 | 10 | 14 | 3 | 8 | 11 |
| Total | 9 | 11 | 20 | 7 | 9 | 16 |
| Accuracy | | 75% | | | 75% | |

Discussion

These results demonstrate the utility of the ChemoFx® assay in predicting treatment for breast cancer, and particular neoadjuvant treatment. The assay was successfully executed on non-surgical tissue obtained from transcutaneous needle biopsies from neoadjuvant breast cancer patients. Historically, CSRAs have required 1-2 g of tissue, which typically necessitates obtaining tissue at the time of surgery. These results demonstrate the ability of the ChemoFx® assay to effectively assess multiple chemotherapy agents on as little as about 35 mg of tissue specimen.

The present results demonstrate the ability of the assay to provide consistent results. Across 10 plates, the coefficient of variance of aAUC was found to be 2.3% for FEC and 2.9% for DF. The lower variability in the process ensures the ability of the ChemoFx® assay to measure the biological heterogeneity of the tumor tissue.

The results of the testing as shown in the heat map analysis (FIG. 3) reflect what you would expect to see clinically—different patients respond differently to the same agent (reading horizontally in FIG. 3). Evidence from cross-over trials of doxorubcin and paclitaxel support this observation (12, 13). Patients also respond differently to various agents (reading vertically in FIG. 3). Based on historical population response rates, the various regimens constituting the current standards of care yield similar expected pathological complete response rates of approximately 20% (1, 2). The clinician may have no indication as to which of those regimens is the best choice for an individual patient. The ability to determine patient response to therapy, as demonstrated herein, provides an opportunity to help oncologists improve patient outcome.

When the ability of the ChemoFx® assay to predict patient outcome was evaluated, it was found that, while blind to the assay results at the time of treatment, the in vitro response correlated with patient response to chemotherapy agents. Although other studies have evaluated chemosensitivity assays in breast cancer, most have been performed on samples acquired at the time of surgery (14-16).

The assay metric aAUC for DF acted as a strong predictor of pCR in patients who underwent sequential regimens of FEC followed by DF. Furthermore, it was the only independent variable measured that demonstrated this predictive ability. Such a finding suggests that DF may be more effective than FEC in achieving pCR. In fact, it was recently reported that docetaxel increased overall clinical response from 57% to 75% when given in 4 cycles following 4 cycles of FEC as neoadjuvant therapy in breast cancer patients (19). However, it is difficult to tease out the effects of individual drugs in studies involving sequential drug regimens.

The strength of these findings is that the formula for predicting response was cross-validated (Table 3B). Since the collaboration with the investigators of the US Oncology 02-103 trial was reached near the end of the study, this study had access to biopsies of only the last 34 patients enrolled. This sample size limited the study from accounting for more covariates in the model. To guard against overfitting, we cross-validated the model by using the leave-one-out cross validation technique. The cross-validated model also yielded a 75% prediction accuracy, the same as the original model, minimizing the likelihood of an over-fit model.

Factors such as stage, grade, and ER, PR, and Her2 status are considered to be prognostic indicators of response. Yet, none of these factors were statistically predictive of pCR here. Higher percentages of patients with Stage III vs Stage II, Grade G2 vs G3, ER and PR negative versus positive status, and Her2 positive versus negative status achieved pCR, but none of these differences were statistically significant. Although our study size was small and may preclude detecting these associations, similar results were reported from a trial of 118 breast cancer patients treated with neoadjuvant therapy (20). In another trial of neoadjuvant chemotherapy for breast cancer in 435 patients, the association of ER negative status with pCR was statistically significant (21). In contrast to our findings however, the highest percentage of patients achieving pCR based on grade occurred in those with Grade III status. Since the choice of neoadjuvant chemotherapy regimen likely affects clinical outcome, reported associations between clinical factors and pCR vary from trial to trial, making valid comparisons difficult.

Nevertheless, clinical factors need to be considered as possible co-predictors or confounders when using assay metrics to correctly predict patient outcome. When we adjusted for clinical factors in our analyses, however, the estimated parameters from model fittings and prediction accuracies did not vary, suggesting that aAUC_DF may be an independent predictor of clinical response.

Chemosensitivity and chemoresistance assays have faced considerable scrutiny over the years. Unlike other chemosensitivity and chemoresistance assays (16, 22-25), the ChemoFx® assay directly counts the number of viable cells remaining after live tissue has been subjected to multiple doses of various chemotherapy drugs. Furthermore, the technology may be automated, thus improving accuracy and minimizing human error. The result is a dose-response curve that more accurately reflects drug cytotoxicity. The present invention transforms information from the curves into an assay metric correlating to patient clinical outcome or to fit prediction models. The adjusted area under the curve has been employed rather than the commonly used EC50 or IC50 approaches (26). By using slope weights at each dose point, the assay is able to avoid curve fitting errors associated with curve irregularity among individual cancer patients. Such an empirical approach may provide robustness to clinical outcome prediction.

The following references are hereby incorporated by reference in their entireties.

REFERENCES

1 Mieog J S, van der Hage J A, and van d, V: Preoperative chemotherapy for women with operable breast cancer. Cochrane Database Syst Rev CD005002, 2007.
2 Sachelarie I, Grossbard M L, Chadha M, Feldman S, Ghesani M, and Blum R H: Primary systemic therapy of breast cancer. Oncologist 11: 574-589, 2006.
3 Pinder S E, Provenzano E, Earl H, and Ellis I O: Laboratory handling and histology reporting of breast specimens from patients who have received neoadjuvant chemotherapy. Histopathology 50: 409-417, 2007.
4 Ness R B, Wisniewski S R, Eng H, and Christopherson W: Cell viability assay for drug testing in ovarian cancer: in vitro kill versus clinical response. Anticancer Res 22: 1145-1149, 2002.
5 Samson D J, Seidenfeld J, Ziegler K, and Aronson N: Chemotherapy sensitivity and resistance assays: a systematic review. J Clin Oncol 22: 3618-3630, 2004.
6 Schrag D, Garewal H S, Burstein H J, Samson D J, Von Hoff D D, and Somerfield MR: American Society of Clinical Oncology Technology Assessment: chemotherapy sensitivity and resistance assays. J Clin Oncol 22: 3631-3638, 2004.
7 Kornblith P, Wells A, Gabrin M J, Piwowar J, George L D, Ochs R L, and Burholt D: Breast cancer—response rates to chemotherapeutic agents studied in vitro. Anticancer Res 23: 3405-3411, 2003.
8 Gallion H, Christopherson W A, Coleman R L, DeMars L, Herzog T, Hosford S, Schellhas H, Wells A, and Sevin BU: Progression-free interval in ovarian cancer and predictive value of an ex vivo chemoresponse assay. Int J Gynecol Cancer 16:194-201, 2006.
9 Parker S H and Klaus A J: Performing a breast biopsy with a directional, vacuum-assisted biopsy instrument. Radiographics 17: 1233-1252, 1997.
10 Nakano S, Sakamoto H, Ohtsuka M, Mibu A, Sakata H, and Yamamoto M: Evaluation and indications of ultrasound-guided vacuum-assisted core needle breast biopsy. Breast Cancer 14: 292-296, 2007.
11 Untch M, Ditsch N, Langer E, Kurbacher C, Crohns C, Konecny G, Kahlert S, Bauerfeind I, and Hepp H: Chemosensitivity testing in gynecologic oncology—dream or reality? Recent Results Cancer Res 161: 146-158, 2003.
12 Sledge G W, Neuberg D, Bernardo P, Ingle J N, Martino S, Rowinsky E K, and Wood WC: Phase III trial of doxorubicin, paclitaxel, and the combination of doxorubicin and paclitaxel as front-line chemotherapy for metastatic breast cancer: an intergroup trial (E1193). J Clin Oncol 21: 588-592, 2003.
13 Paridaens R, Biganzoli L, Bruning P, Klijn J G, Gamucci T, Houston S, Coleman R, Schachter J, Van V A, Sylvester R, Awada A, Wildiers J, and Piccart M: Paclitaxel versus doxorubicin as first-line single-agent chemotherapy for metastatic breast cancer: a European Organization for Research and Treatment of Cancer Randomized Study with cross-over. J Clin Oncol 18: 724-733, 2000.
14 Ellis R J, Fabian C J, Kimler B F, Tawfik O, Mayo M S, Decelis C R, Jewell W R, Connor C, Modrell C, Praeger M, McGinness M, Mehta R, and Fruehauf JP: Factors associated with success of the extreme drug resistance assay in primary breast cancer specimens. Breast Cancer Res Treat 71: 95-102, 2002.
15 Xu J M, Song S T, Tang Z M, Liu X Q, Jiang Z F, Zhou L, Li Y B, and Huang Y: Evaluation of in vitro chemosensitivity of antitumor drugs using the MTT assay in fresh human breast cancer. Breast Cancer Res Treat 49: 251-259, 1998.
16 Xu J M, Song S T, Tang Z M, Jiang Z F, Liu X Q, Zhou L, Zhang J, and Liu X W: Predictive chemotherapy of advanced breast cancer directed by MTT assay in vitro. Breast Cancer Res Treat 53: 77-85, 1999.
17 Xu J M, Song S T, Tang Z M, Jiang Z F, Liu X Q, Zhang J, Liu X W, and Paradiso A: Neoadjuvant chemotherapy in inoperable, locally advanced, and inflammatory breast carcinoma: a pilot study of MTT assay in vitro and outcome analysis of 10 patients. Am J Clin Oncol 24: 259-263, 2001.
18 Lau, G. I. S. T., Loo, W. T. Y., and Chow, L. W. C. Neoadjuvant chemotherapy for breast cancer determined by chemosensitivity assay achieves better tumor response. Biomed. Pharmacother. 2007.
Ref Type: In Press
19 Ohnoa S, Toi M, Kuroi K, Nakamura S, Iwata H, Kusama M, Masuda N, Yamazaki K, Hisamatsu K, Sato Y, Takatsuka Y, Shin E, Kaise H, Kurozumi M, Tsuda H, and Akiyama F: Update results of FEC followed by docetaxel neoadjuvant trials for primary breast cancer. Biomed Pharmacother 59 *Suppl* 2: S323-S324, 2005.
20 Burcombe R J, Makris A, Richman P I, Daley F M, Noble S, Pittam M, Wright D, Allen S A, Dove J, and Wilson G D: Evaluation of ER, PgR, HER-2 and Ki-67 as predictors of response to neoadjuvant anthracycline chemotherapy for operable breast cancer. Br J Cancer 92: 147-155, 2005.
21 Ring A E, Smith I E, Ashley S, Fulford L G, and Lakhani S R: Oestrogen receptor status, pathological complete response and prognosis in patients receiving neoadjuvant chemotherapy for early breast cancer. Br J Cancer 91: 2012-2017, 2004.
22 Von Hoff D D, Kronmal R, Salmon S E, Turner J, Green J B, Bonorris J S, Moorhead E L, Hynes H E, Pugh R E, Belt R J, and: A Southwest Oncology Group study on the use of a human tumor cloning assay for predicting response in patients with ovarian cancer. Cancer 67: 20-27, 1991.
23 Wilbur D W, Camacho E S, Hilliard D A, Dill P L, and Weisenthal L M: Chemotherapy of non-small cell lung carcinoma guided by an in vitro drug resistance assay measuring total tumour cell kill. Br J Cancer 65: 27-32, 1992.
24 Kurbacher C M, Cree I A, Bruckner H W, Brenne U, Kurbacher J A, Muller K, Ackermann T, Gilster T J, Wilhelm L M, Engel H, Mallmann P K, and Andreotti P E: Use of an ex vivo ATP luminescence assay to direct chemotherapy for recurrent ovarian cancer. Anticancer Drugs 9: 51-57, 1998.

25 Kern D H and Weisenthal L M: Highly specific prediction of antineoplastic drug resistance with an in vitro assay using suprapharmacologic drug exposures. J Natl Cancer Inst 82: 582-588, 1990.

26 Gardner S N: A mechanistic, predictive model of dose-response curves for cell cycle phase-specific and -nonspecific drugs. Cancer Res 60: 1417-1425, 2000.

27 Nagourney R: Chemosensitivity and resistance assays: a systematic review? J Clin Oncol 23: 3640-3641, 2005.

28 Schinkothe T, Haeger S, and Gabri MR: Practical guidelines for diagnostic use of in vitro chemosensitivity tests. Anticancer Res 27: 1365-1367, 2007.

The invention claimed is:

1. A method of selecting docetaxel and 5-fluorouracil (DF) as a neoadjuvant chemotherapy predictive of pathological complete response for a breast cancer patient, comprising:
preparing one or more explants for cell culture from a transcutaneous biopsy specimen from the patient;
growing one or more cell monolayers from said explants, the monolayers comprising malignant cells;
exposing cells from said monolayers to docetaxel and 5-fluorouracil (DF), and at a range of concentrations;
measuring a response of the cells to docetaxel and 5-fluorouracil (DF) within said range;
preparing a dose-response curve for docetaxel and 5-fluorouracil (DF);
scoring the sensitivity of the cells to docetaxel and 5-fluorouracil (DF) by calculating an area under said dose-response curve (AUC); and
selecting docetaxel and 5-fluorouracil (DF) as the neoadjuvant chemotherapy when the cells exhibit sensitivity to docetaxel and 5-fluorouracil (DF).

2. The method of claim 1, wherein the breast cancer patient has stage II or stage III breast cancer.

3. The method of claim 1, wherein said transcutaneous biopsy specimen is one or more core needle biopsies.

4. The method of claim 1, wherein the transcutaneous biopsy specimen contains from about 25 mg to about 100 mg of tumor tissue.

5. The method of claim 1, wherein the transcutaneous biopsy specimen contains from about 10 mg to about 50 mg of tumor tissue.

6. The method of claim 1, wherein the explants are prepared by mincing tissue from the biopsy specimen.

7. The method of claim 6, wherein said explant has a size of about 0.5 to about 1.5 mm$^3$.

8. The method of claim 7, wherein the tissue is not exposed to enzymatic treatment.

9. The method of claim 1, wherein said monolayer contains at least 65% epithelial cells.

10. The method of claim 1, wherein said monolayer contains at least 75% epithelial cells.

11. The method of claim 1, wherein the cells of said monolayer are suspended prior to confluency, and seeded for testing.

12. The method of claim 11, wherein the cells of said monolayer are seeded in wells of one or more microtiter plate(s).

13. The method of claim 1, wherein measuring the response of the cells comprises measuring cell growth or cell death.

14. The method of claim 1, wherein sensitivity or resistance to docetaxel and 5 fluorouracil is determined by comparing the AUC score to a cut-off value.

15. The method of claim 1, wherein the method is fully or partially automated.

16. A method of selecting docetaxel and 5-fluorouracil (DF) as a neoadjuvant chemotherapy predictive of pathological complete response for a breast cancer patient, comprising:
preparing one or more explants for cell culture from a transcutaneous biopsy specimen from the patient;
growing one or more cell monolayers from said explants, the monolayers comprising malignant cells;
exposing cells from said monolayers to docetaxel and 5-fluorouracil (DF), and at a range of concentrations;
measuring a response of the cells to docetaxel and 5-fluorouracil (DF) within said range;
preparing a dose-response curve for docetaxel and 5-fluorouracil (DF);
scoring the sensitivity of the cells to docetaxel and 5-fluorouracil (DF) by calculating an area under said dose-response curve (AUC); and
and selecting docetaxel and 5-fluorouracil (DF) as the neoadjuvant chemotherapy when the cells exhibit sensitivity to docetaxel and 5-fluorouracil (DF).

17. The method of claim 16, wherein the changes in cytotoxicity between dose points along the dose-response curve are represented by a local slope, and the local slope is weighted along the dose-response curve to emphasize cytotoxicity.

18. The method of claim 17, wherein the AUC is determined by:
calculating the local slope at a plurality of dose points;
weighting the local slopes to emphasize the level of cell toxicity at said plurality of dose points; and
calculating an AUC that incorporates the weighted local slopes.

* * * * *